United States Patent
Kim et al.

(10) Patent No.: US 8,901,088 B2
(45) Date of Patent: Dec. 2, 2014

(54) **COMPOSITION FOR PREVENTING OR TREATING POLIOSIS OR VITILIGO COMPRISING A *PUERARIA* GENUS PLANT EXTRACT OR PUERARIN**

(75) Inventors: Hyoung-Jun Kim, Yongin-si (KR); Won Seok Park, Seoul (KR); Hyun Ju Koh, Anyang-si (KR); Dae-Jin Min, Seoul (KR); Nok Hyun Park, Seongnam-si (KR); Pil Joon Park, Yongin-si (KR); Su Na Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 140 days.

(21) Appl. No.: 13/582,110

(22) PCT Filed: Mar. 4, 2010

(86) PCT No.: PCT/KR2010/001360
§ 371 (c)(1),
(2), (4) Date: Aug. 31, 2012

(87) PCT Pub. No.: WO2011/108774
PCT Pub. Date: Sep. 9, 2011

(65) Prior Publication Data
US 2012/0329739 A1 Dec. 27, 2012

(51) Int. Cl.
*A61K 8/60* (2006.01)
*A61Q 5/00* (2006.01)
*A61Q 19/04* (2006.01)
*A61Q 5/10* (2006.01)
*A61K 8/97* (2006.01)

(52) U.S. Cl.
CPC *A61Q 5/10* (2013.01); *A61Q 19/04* (2013.01); *A61K 8/97* (2013.01)
USPC .......................................................... 514/27

(58) Field of Classification Search
CPC ............ A61K 8/97; A61Q 19/04; A61Q 5/10
USPC .......................................................... 514/27
See application file for complete search history.

(56) References Cited

U.S. PATENT DOCUMENTS

| 5,639,785 | A | 6/1997 | Kung | |
| 2004/0105900 | A1* | 6/2004 | Cherdshewasart | 424/725 |
| 2005/0196475 | A1* | 9/2005 | D'Amelio et al. | 424/757 |

FOREIGN PATENT DOCUMENTS

| CN | 1586297 A | | 3/2005 |
| CN | 101507698 A | | 8/2009 |
| JP | 64-16709 A | | 1/1989 |
| KR | 10-2009-0066824 A | | 6/2009 |
| KR | 1020090066824 | * | 6/2009 |

OTHER PUBLICATIONS

Glossary of medical education terms, Institute of International Medical Education. http://www.iime.org/glossary.htm Accessed in Mar. 2013.*
Trueb R. Pharmacologic interventions in aging hair. Clin Intervent Aging 1:121-129, 2006.*
Szczurko et al. A systematic review of natural health product treatment for vitiligo. BMC Dermotol 8:2, 2008.*
Keung et al. Kudzu Root: An Ancient Chinese Source of Modern Antidipsotropic Agents. Phytochemistry 47:499-506, 1998.*
"Jeongjangsam, a Study of Pharmacology and Clinical Application of *Pueraria*," Shenzhen Journal of Integrated Traditional Chinese and Western Medicine, vol. 11, No. 4, pp. 246-249, Aug. 2001.
Anthony C. Dweck, "Isoflavones, Phytohormones and Phytosterols," J. Appl. Cosmetol, vol. 24, pp. 17-21, Jan./Mar. 2006.

* cited by examiner

*Primary Examiner* — Brandon Fetterolf
*Assistant Examiner* — Yih-Horng Shiao
(74) *Attorney, Agent, or Firm* — Dickstein Shapiro LLP

(57) ABSTRACT

Disclosed is a composition for preventing or treating poliosis or vitiligo comprising a *Pueraria* genus plant extract or puerarin as an active ingredient.

7 Claims, 3 Drawing Sheets

COMPOSITION FOR PREVENTING OR TREATING POLIOSIS OR VITILIGO COMPRISING A *PUERARIA* GENUS PLANT EXTRACT OR PUERARIN

TECHNICAL FIELD

The present disclosure relates to a composition for preventing or treating poliosis or vitiligo.

BACKGROUND ART

Since hair graying occurring with aging gives a strong impression of old age, hairdyes for concealing gray hair have been studied a lot. However, hair dyeing is only a makeshift measure since gray hair grows again. Further, the currently used oxidative hairdyes damage the skin since they contain oxidizing agents.

For inhibition of hair graying, a composition by mixing black sesame, walnut, herba ecliptae, honey mixed with rehmanniae radix preparata, asparagi radix or liriopes radix, a liquid obtained by boiling polygoni multiflori radix, thuja leaf, ligustri lucidi fructus, herba ecliptae, rock salt, rehmanniae radix preparata, asparagi radix, liriopes radix and black bean at 50° C. is often used. Also, black sesame, black pine leaf, kelp, acanthopanacis cortex extract, pituitary hormone, cyclic adenosine monophosphate (cAMP) or vitamin $D_3$ is used, but the effect is not so significant.

DISCLOSURE

Technical Problem

The present disclosure is directed to providing a composition for preventing or treating hair graying or vitiligo.

Technical Solution

In one general aspect, the present disclosure provides a composition for preventing or treating hair graying comprising an extract of a plant in the genus *Pueraria* as an active ingredient.

In another general aspect, the present disclosure provides a composition for preventing or treating vitiligo comprising an extract of a plant in the genus *Pueraria* as an active ingredient.

In another general aspect, the present disclosure provides a composition for preventing or treating hair graying comprising puerarin as an active ingredient.

In another general aspect, the present disclosure provides a composition for preventing or treating vitiligo comprising puerarin as an active ingredient.

Advantageous Effects

The composition comprising an extract of a plant in the genus *Pueraria* or puerarin as an active ingredient provided by the present disclosure has an effect of preventing or treating hair graying or vitiligo by increasing the expression of the microphthalmia-associated transcription factor (MITF) in melanocytes, thus activating melanocytes and promoting melanin synthesis.

BEST MODE

Figure 1:
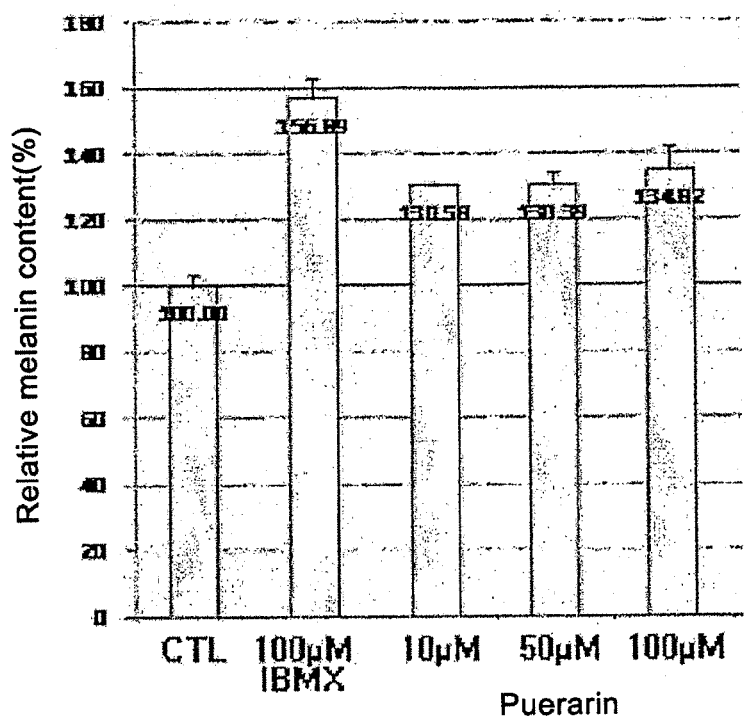
FIG. 1 shows a result of comparing puerarin's melanin synthesis effect with a positive control and a negative control in Test Example 1.

As used herein, "skin" means the tissue covering the body surface of an animal and is used in the broadest sense, including not only the tissue that covers the face or body but also the scalp and hair.

As used herein, "hair" includes both body hair and head hair. The hair includes both human's and animal's hair.

As used herein, "extract" means a substance extracted from a natural substance, regardless of the extracted method or ingredients. The term is used in a broad sense including, for example, ingredients soluble in water or an organic solvent extracted from a natural substance using the solvent, or specific ingredients of a natural substance such as oil extracted therefrom.

Hereinafter, the present disclosure is described in further detail.

Hair graying is known to be caused by loss of melanocyte stem cells and decreased activity of melanocytes. In particular, aging-associated hair graying is known to be mainly caused by the loss of stem cells, whereas hair graying not associated with aging is known to be caused by decreased activity of melanocytes owing to environmental and mental stresses in modern society.

In an aspect of the present disclosure, an extract of one or more plant in the genus *Pueraria* includes an extract of one or more general plant in the genus *Pueraria* of the family Leguminosae. In another aspect of the present disclosure, an extract of one or more plant in the genus *Pueraria* is selected from *Pueraria mirifica, Pueraria tuberosa* (Roxb. ex Willd) DC., *Pueraria thomsonii* Benth, *Pueraria thunbergiana* Benth, *Pueraria peduncularis* Grah, *Pueraria omeiensis* Wang et Tang, *Pueraria phaseoloides* (Roxb.) Benth, *Pueraria montana* (Lour.) Merr and *Pueraria edulis* Pamp.

In an aspect of the present disclosure, the extract of the plant in the genus *Pueraria* may be obtained by extracting the plant in the genus *Pueraria* according to a commonly employed method. In another aspect of the present disclosure, the extract of the plant in the genus *Pueraria* may be obtained by extracting the plant in the genus *Pueraria* using water or an organic solvent including alcohol under controlled temperature and pressure. In an aspect, the organic solvent is not particularly limited and may be a $C_1$-$C_5$ lower alcohol. The $C_1$-$C_5$ lower alcohol may be, for example, at least one selected from a group consisting of methanol, ethanol, isopropyl alcohol, n-propyl alcohol, n-butanol and isobutanol.

In an aspect of the present disclosure, the extract of the plant in the genus *Pueraria* comprises miroesterol, daidzin, daidzein, genistin, genistein, puerarin, β-sitosterol, stigmasterol, coumestrol, mirificoumestan, mirificine, campesterol or kwakhurin. In another aspect of the present disclosure, the extract of the plant in the genus *Pueraria* comprises puerarin as an active ingredient.

The puerarin is an isoflavone and is the 8-glucoside of daidzein.

The chemical formula of puerarin is given in Chemical Formula 1, and may be expressed as daidzein-8-C-glucopyranoside, 8-C-β-D-glucopyranosyl-4',7-dihydroxyisoflavone, or 8-C-β-D-glucopyranosyl-7-hydroxy-3-(4-hydroxyphenyl)-4H-1-benzopyran-4-one.

Chemical Formula 1

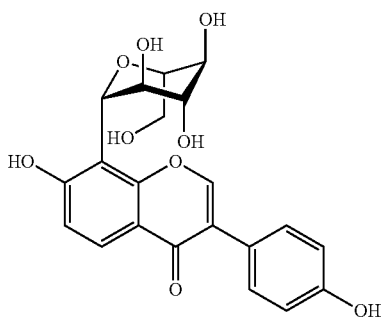

In an aspect of the present disclosure, the puerarin may be obtained from the nature or be synthesized. In the nature, it is present mainly in the root of the plants in the genus *Pueraria*, family Leguminosae. In an aspect of the present disclosure, the puerarin may be obtained from a plant belonging to the genus *Pueraria* of the family Leguminosae. In another aspect of the present disclosure, the puerarin may be obtained from a plant in the genus *Pueraria* including *Pueraria mirifica, Pueraria tuberosa* (Roxb. ex Willd) DC., *Pueraria thomsonii* Benth, *Pueraria thunbergiana* Benth, *Pueraria peduncularis* Grah, *Pueraria omeiensis* Wang et Tang, *Pueraria phaseoloides* (Roxb.) Benth, *Pueraria montana* (Lour.) Merr, *Pueraria edulis* Pamp and *Pueraria lobata* (Willd.) Ohwi.

The melanin synthesis activity of melanocytes is greatly affected by the microphthalmia-associated transcription factor (MITF). A composition comprising an extract of a plant in the genus *Pueraria* or puerarin is effective in promoting melanin production by facilitating the expression of MITF in melanocytes. That is to say, in an aspect of the present disclosure, a composition comprising an extract of the plant in the genus *Pueraria* or puerarin as an active ingredient may prevent or treat hair graying or vitiligo by inducing melanin synthesis through remarkably enhanced expression of MITF in melanocytes.

In an aspect of the present disclosure, the composition comprising the extract of the plant in the genus *Pueraria* or puerarin as an active ingredient may comprise the extract of the plant in the genus *Pueraria* or puerarin in an amount of 0.1-10 wt % based on the total weight of the composition. In another aspect of the present disclosure, the composition comprising the extract of the plant in the genus *Pueraria* or puerarin as an active ingredient may comprise the extract of the plant in the genus *Pueraria* or puerarin in an amount of 0.1-5 wt % based on the total weight of the composition. In another aspect of the present disclosure, the composition comprising the extract of the plant in the genus *Pueraria* or puerarin as an active ingredient may comprise the extract of the plant in the genus *Pueraria* or puerarin in an amount of 0.1-2.5 wt % based on the total weight of the composition. When the extract of the plant in the genus *Pueraria* or puerarin is comprised in an amount of 0.1-10 wt % based on the total weight of the composition, the intended effect of the present disclosure can be adequately achieved while both stability and safety are satisfied and favorable cost-effectiveness is achieved.

In an aspect of the present disclosure, the composition comprising the extract of the plant in the genus *Pueraria* or puerarin as an active ingredient may be for application on the hair or scalp of the head. In another aspect of the present disclosure, the composition comprising the extract of the plant in the genus *Pueraria* or puerarin as an active ingredient may be for application on the skin.

In an aspect, the present disclosure provides a beauty care composition comprising the extract of the plant in the genus *Pueraria* or puerarin as an active ingredient. The beauty care composition may be a cosmetic composition. The cosmetic composition may comprise a cosmetologically or dermatologically allowable medium or base. It may be provided in any topically applicable form including, for example, solution, gel, solid, anhydrous slurry, oil-in-water emulsion, water-in-oil emulsion, multiemulsion, suspension, microemulsion, microcapsule, microgranule, ionic (liposome) or non-ionic vesicular dispersion, cream, toner, lotion, powder, ointment, spray, cleanser or conceal stick. Also, the composition according to the present disclosure may be used in the form of foam, an aerosol composition further comprising a pressurized propellant, or patch. Such compositions may be prepared by a method commonly employed in the art.

The cosmetic composition may further comprise other ingredients providing synergic effect without negatively affecting the desired effect. Those skilled in the art will select those ingredients without difficulty considering the preparation form or purpose of use of the cosmetic composition.

For example, the cosmetic composition may comprise a skin absorption enhancer in order to enhance the desired effect. Also, the cosmetic composition of the present disclosure may comprise a substance selected from a group consisting of water-soluble vitamin, oil-soluble vitamin, polymer peptide, polymer polysaccharide, sphingolipid and seaweed extract. The cosmetic composition of the present disclosure may further comprise other ingredients, which are mixed in typical cosmetic compositions, in addition to the active ingredient. The other ingredients which can be added may include oil, fat, moisturizing agent, emollient agent, surfactant, organic or inorganic pigment, organic powder, ultraviolet absorbent, antiseptic, fungicide, antioxidant, plant extract, pH adjuster, alcohol, colorant, flavor, blood circulation accelerant, cooling agent, antiperspirant, purified water, or the like. The ingredients that can be included in the cosmetic composition are not restricted to those described above, and their contents may be determined within ranges not deteriorating the purpose and the effect of the present disclosure.

The cosmetic composition is not particularly limited with regard to the formulation thereof and the formulation may be determined appropriately depending on purposes. For example, the cosmetic composition may be provided as one or more formulation selected from a group consisting of softening lotion, nourishing lotion, essence, nourishing cream, massage cream, pack, gel, makeup base, foundation, powder, lipstick, patch, spray, eye cream, eye essence, cleansing cream, cleansing foam, cleansing water, cleanser, hair shampoo, hair conditioner, hair treatment product, hair essence, hair lotion, scalp/hair tonic, scalp essence, hair gel, hair spray, hair pack, body lotion, body cream, body oil and body essence, but is not limited thereto.

In an aspect, the present disclosure provides a pharmaceutical composition comprising the extract of the plant in the genus *Pueraria* or puerarin as an active ingredient. The pharmaceutical composition may further comprise, in addition to the active ingredient, a pharmaceutical adjuvant such as antiseptic, stabilizer, wetting agent, emulsifying accelerator, salt and/or buffer for controlling osmotic pressure, diluent (for example, lactose, dextrose, sucrose, mannitol, sorbitol, cellulose or glycine), lubricant (for example, silica, talc, stearic acid and magnesium or calcium salt thereof or polyethylene glycol), binder (for example, magnesium aluminum silicate, starch paste, gelatin, tragacanth, methyl cellulose, sodium carboxymethyl cellulose or polyvinylpyrrolidone) or the like, or other therapeutically useful substance. If necessary, other pharmaceutical additives, for example, disintegrant such as starch, agar, alginic acid or a sodium salt thereof, absorbent, colorant, flavor, sweetener, or the like, may be further included.

The pharmaceutical composition may be prepared into various formulations for oral or parenteral administration. Formulations for parenteral administration may include, for example, drop, ointment, lotion, gel, cream, spray, suspension, emulsion, suppository, patch or the like, but are not limited thereto.

In an aspect of the present disclosure, the pharmaceutical composition may be administered orally, parenterally, topically or transdermally.

The dose of the active ingredient may be varied with the age, sex and body weight of a subject to be treated, particular disease or pathological condition be treated, severity of the disease or pathological condition, administration route and the judgment of a prescriber. Determination of the dose considering these factors is within the level of those skilled in the art. In general, the dose may be 0.001-2000 mg/kg/day, more specifically 0.5-500 mg/kg/day.

In an aspect, the present disclosure provides a health food composition comprising the extract of the plant in the genus *Pueraria* or puerarin as an active ingredient. The health food composition may be formulated into, for example, tablet, granule, drink, caramel, diet bar, or the like. Each formulation of the health food composition may comprise, in addition to the active ingredient, ingredients which are commonly used in the art. The ingredients may be selected by those skilled in the art without difficulty considering the purpose of use and may provide a synergic effect.

MODE FOR INVENTION

The features and effects of the present disclosure will be described in detail through test examples. However, the following test examples are provided for illustrative purposes only and are not intended to limit the scope of the present disclosure.

Test Example 1

Evaluation of Melanin Synthesis Promoting Effect

In order to evaluate the puerarin's effect of promoting melanin synthesis, melan-A melanocytes ($5.0 \times 10^4$) are introduced to a 24-well plate and cultured overnight at 37° C. under 10% $CO_2$ atmosphere. The culture is treated with puerarin diluted to 10 μM, 50 μM or 100 μM in RPMI medium containing 10% FBS and TPA. The same experiment is carried out without treatment as negative control (CTL) or by treating with 100 μM isobutylmethylxanthine (IBMX) as positive control. 5 days later, melanin in the cells is dissolved in 1 N NaOH and protein is quantitated by the Lowry method. Absorbance is measured at 405 nm and melanin content is calculated therefrom.

FIG. 1 shows the melanin content of the positive control group and test groups relative to the melanin content of the negative control group.

As seen from FIG. 1, puerarin is effective in promoting melanin synthesis since the melanin content is higher than the negative control group. It can be seen that the melanin synthesis promoting effect is concentration-dependent.

Test Example 2

Evaluation of Hair Graying Preventing Effect of Extract of Plant in the Genus *Pueraria* and Puerarin The hair graying preventing effect is tested as follows using hair graying-induced mice ($Mitf^{mi-vit}$) purchased from the Jackson Lab (USA). The mice experience hair graying with time since melanin synthesis in the hair follicle decreases. 10-week-old female mice are depilated under anesthesia to induce entry into the growth phase. The area of depilation is constant for all individual mice. From the next day, 0.1 mL of test substance or negative control substance is applied on the depilated area, twice a day. This procedure is performed for 3 weeks, 5 times a week.

The test substances are 1% puerarin composition and 1% *Pueraria mirifica*, *Pueraria tuberosa* (Roxb. ex Willd) DC., *Pueraria thomsonii* Benth, *Pueraria thunbergiana* Benth, *Pueraria peduncularis* Grah, *Pueraria omeiensis* Wang et Tang, *Pueraria phaseoloides* (Roxb.) Benth, *Pueraria montana* (Lour.) Merr and *Pueraria edulis* Pamp extracts. As the vehicle for the test substances, a mixture of EtOH, 1,3-BG and DW (v/v/v=3:2:5) is used. And, the vehicle itself is used as the negative control substance.

3 weeks later, hairs are collected from the test area of the mice and melanin content is measured. The melanin content can be measured by treating the hairs with Tris buffer containing the protease Esperase (Novozymes) and then measuring absorbance at 400 nm.

Figure 2:
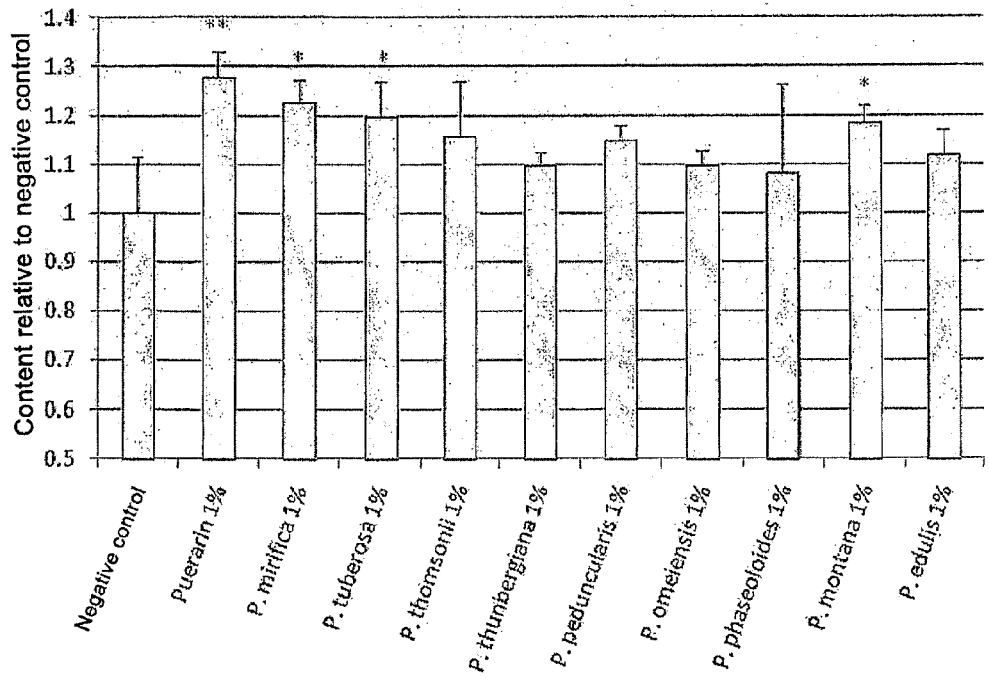
FIG. 2 shows a result of applying a negative control substance, puerarin or an extract of a plant in the genus *Pueraria* to a hair graying-induced mouse model and measuring melanin content in Test Example 2 (*: $p<0.1$, **: $p<0.05$).

FIG. 2 shows a result of applying the negative control substance or the test substances for 3 weeks and then measuring melanin content.

As seen from FIG. 2, the groups treated with puerarin or the extract of the plant in the genus *Pueraria* show higher melanin content. Accordingly, it can be seen that they are effective in increasing melanin content in the hairs of the hair graying-induced mice and thus preventing hair graying.

Test Example 3

Evaluation of Hair Graying Preventing Effect of Puerarin

The hair graying preventing effect is tested in a manner similar to that in Test Example 2 using hair graying-induced mice ($Mitf^{mi-vit}$) purchased from the Jackson Lab (USA). 10-week-old male and female mice are depilated under anesthesia to induce entry into the growth phase. The area of depilation is constant for all individual mice. From the next day, 0.1 mL of test substance, positive control substance or negative control substance is applied on the depilated area, twice a day. This procedure is performed for 3 weeks, 5 times a week.

The test substances are 0.5% and 1% puerarin compositions. As the vehicle for the test substances, a mixture of EtOH, 1,3-BG and DW (v/v/v=3:2:5) is used. The vehicle itself is used as the negative control substance, and 50 mM IBMX (1.1%) is used as the positive control substance.

3 weeks later, hairs are collected from the test area of the mice and melanin content is measured. The melanin content can be measured by treating the hairs with Tris buffer containing the protease Esperase (Novozymes) and then measuring absorbance at 400 nm.

Figure 3:
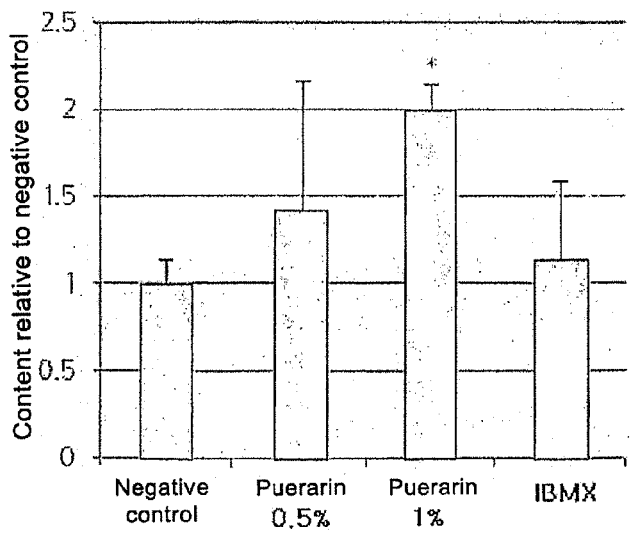
FIG. 3 shows a result of applying a positive control substance, a negative control substance or 0.5% or 1% puerarin to a hair graying-induced male mouse model and measuring melanin content in Test Example 3 (*: $p<0.1$).
Figure 4:
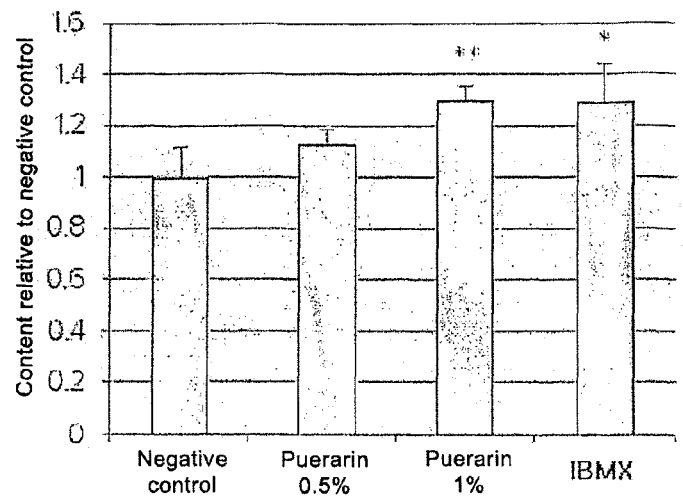
FIG. 4 shows a result of applying a positive control substance, a negative control substance or 0.5% or 1% puerarin to a hair graying-induced female mouse model and measuring melanin content in Test Example 3 (*: $p<0.1$, **: $p<0.05$).
Figure 5:
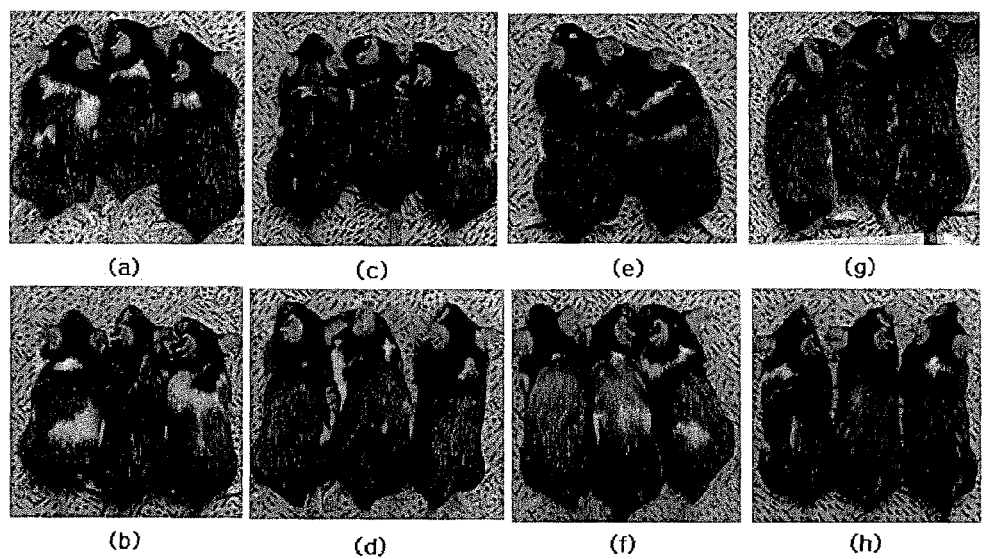
FIG. 5 shows images photographed after applying a positive control substance, a negative control substance or 0.5% or 1% puerarin to mice in Test Example 3. (a), (b): negative control substance was applied to male and female mice; (c), (d): 0.5% puerarin composition was applied to male and female mice; (e), (f): 1% puerarin composition was applied to male and female mice; (g), (h) a positive control substance was applied to male and female mice.

FIG. 3 shows a result of applying the positive control substance (IBMX), the negative control substance or the test substances for 3 weeks to the hair graying-induced male mice and then measuring melanin content. FIG. 4 shows a result of applying the positive control substance, the negative control substance or the test substances for 3 weeks to the hair graying-induced female mice and then measuring melanin content. FIG. 5 shows images photographed after applying the positive control substance, the negative control substance or the test substances for 3 weeks to the male and female mice. In FIG. 5, (a) and (b) show the result of applying the negative control substance to the male and female mice, (c) and (d) show the result of applying the 0.5% puerarin composition to the male and female mice, (e) and (f) show the result of applying the 1% puerarin composition to the male and female mice, and (g) and (h) show the result of applying the positive control substance to the male and female mice.

As seen from FIGS. 3 to 5, puerarin is effective in increasing melanin content in the hairs of the hair graying-induced mice, both male and female, and thus in preventing hair graying. Also, it can be seen that the effect increases as the concentration of puerarin increases.

Formulation examples of the composition according to the present disclosure are described hereinafter. However, other formulations are also possible and the scope of the present disclosure is not limited to the following examples.

Formulation Example 1

Hair Shampoo

TABLE 1

| Ingredients | wt % |
| --- | --- |
| Sodium lauryl sulfate solution (30%) | 20.0 |
| Coconut fatty acid diethanolamide | 5.0 |
| Polyquaternium-10 | 0.3 |
| Propylene glycol | 2.0 |
| Extract of plant in the genus *Pueraria* or puerarin | 0.1-2.5 |
| Piroctone olamine | 0.5 |
| Yellow 203 | adequate |
| p-Oxybenzoic acid ester | 0.2 |
| Combined flavor | adequate |
| Citric acid | adequate |
| Purified water | balance |

Formulation Example 2

Hair Conditioner

TABLE 2

| Ingredients | wt % |
| --- | --- |
| Cetyl trimethyl ammonium chloride (29%) | 7.0 |
| Distearyl dimethyl ammonium chloride (75%) | 4.0 |
| Cetostearyl alcohol | 3.5 |
| Polyoxyethylene stearyl ester | 1.0 |
| Liquid paraffin | 2.0 |
| Propylene glycol | 1.5 |
| Extract of plant in the genus *Pueraria* or puerarin | 0.1-2.5 |
| Combined flavor | adequate |
| Citric acid | adequate |
| Purified water | balance |

Formulation Example 3

Scalp/Hair Tonic

TABLE 3

| Ingredients | wt % |
| --- | --- |
| Menthol | 0.1 |
| D-Panthenol | 0.6 |
| Salicylic acid | 0.05 |
| Glycerin | 1.0 |
| Polyoxyethylene hydrogenated castor oil | 0.8 |
| Tocopheryl acetate | 0.03 |
| Combined flavor | adequate |
| Extract of plant in the genus *Pueraria* or puerarin | 0.1-2.5 |
| Ethanol | 30.0 |
| Purified water | balance |

Formulation Example 4

Scalp Essence

TABLE 4

| Ingredients | wt % |
| --- | --- |
| Ethanol | 30.0 |
| Polysorbate 60 | 1.5 |
| Glycerin | 3.0 |
| Carboxyvinyl polymer | 0.1 |
| Triethanolamine | 0.2 |
| Extract of plant in the genus *Pueraria* or puerarin | 0.1-2.5 |
| Antiseptic | adequate |
| Flavor and colorant | adequate |
| Purified water | balance |

Formulation Example 5

Ointment

TABLE 5

| Ingredients | wt % |
| --- | --- |
| Capric/caprylic triglyceride | 10 |
| Liquid paraffin | 10 |
| Sorbitan sesquiolate | 6 |
| Octyldodeceth-25 | 9 |
| Cetyl ethylhexanoate | 10 |
| Squalane | 1 |
| Salicylic acid | 1 |
| Glycerin | 15 |

TABLE 5-continued

| Ingredients | wt % |
|---|---|
| Sorbitol | 1 |
| Extract of plant in the genus *Pueraria* or puerarin | 2 |
| Antiseptic, colorant and flavor | adequate |
| Purified water | balance |

Formulation Example 6

Lotion

TABLE 6

| Ingredients | wt % |
|---|---|
| Extract of plant in the genus *Pueraria* or puerarin | 0.1-2.5 |
| Beeswax | 4.0 |
| Polysorbate 60 | 1.5 |
| Sorbitan sesquiolate | 1.5 |
| Liquid paraffin | 0.5 |
| Capric/caprylic triglyceride | 5.0 |
| Glycerin | 3.0 |
| Butylene glycol | 3.0 |
| Propylene glycol | 3.0 |

Formulation Example 7

Tablet

TABLE 7

| Ingredients | wt % |
|---|---|
| Extract of plant in the genus *Pueraria* or puerarin | 0.1-2.5 |
| Magnesium stearate | 2.0 |

TABLE 7-continued

| Ingredients | wt % |
|---|---|
| Vitamin C | 2.0 |
| Cornstarch | 50.0 |
| Lactose | balance |

The invention claimed is:

1. A method for treating hair graying in a subject in need thereof, comprising: administering to the subject an effective amount of a composition comprising 0.1-10% by weight of a puerarin based on a total weight of the composition to treat the subject's hair graying.

2. The method according to claim 1, wherein the puerarin is administered to the subject orally, parenterally, topically or transdermally.

3. The method according to claim 1, wherein the puerarin is obtained from one or more plants selected from the group consisting of *Pueraria tuberosa* (Roxb. ex Willd) DC., *Pueraria thomsonii* Benth, *Pueraria thunbergiana* Benth, *Pueraria peduncularis* Grah, *Pueraria omeiensis* Wang et Tang, *Pueraria phaseoloides* (Roxb.) Benth, *Pueraria montana* (Lour.) Merr and *Pueraria edulis* Pamp.

4. The method according to claim 1, wherein the composition comprises the puerarin in an amount of 0.1-5 wt % based on the total weight of the composition.

5. The method according to claim 1, wherein the composition comprises the puerarin in an amount of 0.1-2.5 wt % based on the total weight of the composition.

6. The method according to claim 1, wherein the effective amount is about 0.001-2000 mg/kg/day.

7. The method according to claim 1, wherein the effective amount is about 0.05-500 mg/kg/day.

* * * * *